United States Patent [19]

Sienkiewicz et al.

[11] Patent Number: 4,769,217
[45] Date of Patent: Sep. 6, 1988

[54] APPARATUS FOR MEASURING CONTENT OF ORGANIC CARBON

[75] Inventors: Peter M. Sienkiewicz, Randolph; Roger Mavrides, Norwood, both of Mass.

[73] Assignee: Servomex Company, Norwood, Mass.

[21] Appl. No.: 728,488

[22] Filed: Apr. 29, 1985

[51] Int. Cl.$^4$ .................. G01N 1/10; G01N 27/00
[52] U.S. Cl. ........................... 422/80; 422/82; 422/100; 422/106; 436/146; 436/180; 73/1 H; 73/304 R; 141/198; 141/331; 137/392; 137/428; 222/64; 222/425
[58] Field of Search ............... 73/304 R, 1 H; 141/95, 141/198, 331; 222/56, 61, 64, 425, 424.5; 340/620; 422/80, 81, 82, 100, 106, 110; 436/145, 146, 180; 137/392, 428; 55/215, 218; 220/371

[56] References Cited

U.S. PATENT DOCUMENTS

| | | | |
|---|---|---|---|
| 2,385,161 | 9/1945 | Pinkerton | 340/620 |
| 3,004,554 | 10/1961 | Ziebolz | 137/428 |
| 3,119,266 | 1/1969 | Atkinson | 73/304 R |
| 3,477,460 | 11/1969 | Dotto | 340/620 |
| 3,888,382 | 6/1975 | Blumhardt | 220/371 |
| 3,929,411 | 12/1975 | Takano et al. | 436/43 |
| 3,958,941 | 5/1976 | Regan | 422/80 |
| 4,277,438 | 7/1981 | Ejzak | 422/80 |
| 4,315,579 | 2/1982 | Martin, Jr. | 220/371 |
| 4,362,033 | 12/1982 | Young | 222/56 |
| 4,420,094 | 12/1983 | Chapin | 220/371 |
| 4,483,463 | 11/1984 | Buschmann | 222/64 |
| 4,530,370 | 7/1985 | Horky | 137/205 |
| 4,554,255 | 11/1985 | Ishii et al. | 222/56 |

FOREIGN PATENT DOCUMENTS

83/00207   1/1983   PCT Int'l Appl. .................. 222/56

Primary Examiner—Barry S. Richman
Assistant Examiner—Lynn M. Kummert
Attorney, Agent, or Firm—Marjama & Pincelli

[57] ABSTRACT

An apparatus for automatically selectively introducing successive samples of a liquid from at least one pressurized line into a receiving funnel having an outlet port and at least one inlet port. The receiving funnel has main receiving chamber for receiving liquid samples and a sensing device is also provided in the receiving funnel for sensing the level of liquid present in the receiving funnel for controlling flow in and out of the funnel.

7 Claims, 4 Drawing Sheets

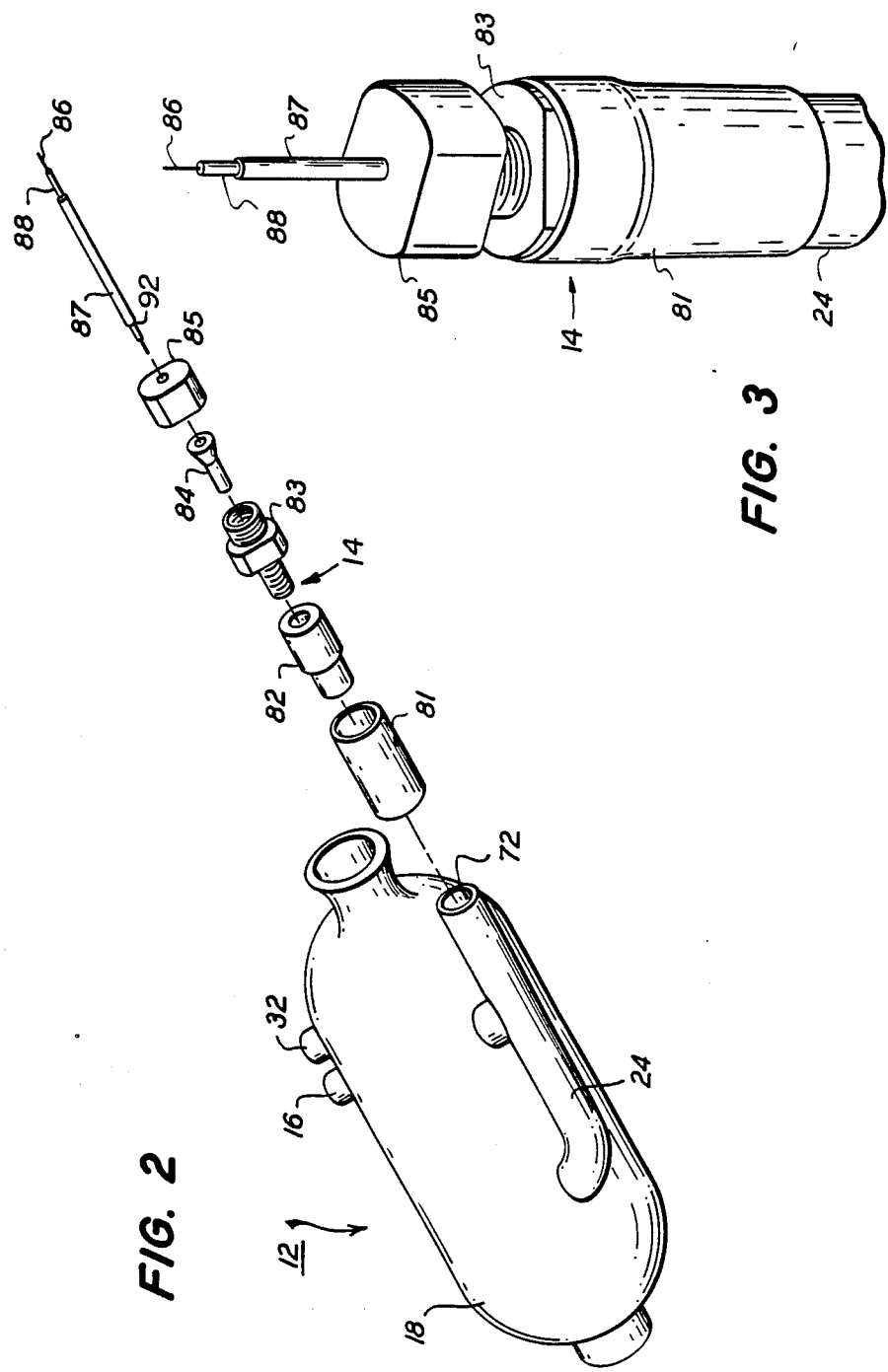

APPARATUS FOR MEASURING CONTENT OF ORGANIC CARBON

The foregoing abstract is not to be taken as limiting the invention of this application, and it in order to understand the full nature and extent of the technical disclosure of this application reference must be made to accompany drawings and the following detailed description.

BACKGROUND OF THE INVENTION

This invention is directed to an improved method and apparatus for measuring organic carbon in an aqueous solution. More particularly, the present invention is directed to an improved method and apparatus for automatically selectively introducing successive samples of a liquid from at least one pressurized line into an apparatus for measuring the content of organic carbon.

Prior art type carbon analyzers have generally been limited to devices having means for manually introducing single samples of an aqueous solution to be analyzed. A example of such a device is described in U.S. Pat. No. 3,958,941 which is owned by assignee of the present invention. In the apparatus described U.S. Pat. No. 3,958,941, a syringe is used to introduce a sample through a rubber septum. It is also known in the prior art to analyze a plurality of samples disposed in individual test tubes. One such device is called Photochem Autosampler and is produced by Analytical Products of the Sybron Corporation. Both of these methods have the disadvantage of having to be performed, at least to some extent, manually and having the potential of introducing impurities into the system thereby causing false measurements.

There also exists in the prior art metering pumps or sample loops for introducing individual sample quantitites into an organic carbon analyzer. However, these systems have the disadvantage of having relatively high initial cost and maintenance or have relatively low reliability, accuracy and efficiency.

Applicants have invented an improved method and apparatus having relatively low cost, simple structure, accurate in dispensing amounts of sample while minimizing the introduction of any impurities to the measuring system.

SUMMARY OF THE INVENTION

The method and apparatus for automatically selectively introducing successive samples of a liquid from at least one pressurized feedline into a receiving funnel having an outlet port and at least one inlet port. The funnel has a main receiving chamber for receiving the liquid sample through said inlet port. Means are provided for emptying and maintaining liquid in said funnel and for controlling the flow of liquid into the funnel. Means are also provided for sensing the level of the liquid sample present in the receiving funnel.

BRIEF DESCRIPTION OF THE DRAWINGS

FIG. 2 is a enlarged exploded assembly view of the funnel illustrated in FIG. 1; and FIG. 3 is enlarged fragment view of a portion of the funnel of FIG. 3 as shown in the assembled state.

While the present invention will be described in connection with a preferred embodiment and method, it will be understood that it is not intended to limit the invention to the embodiment and method so described.

DETAILED DESCRIPTION OF THE INVENTION

Figure 1:
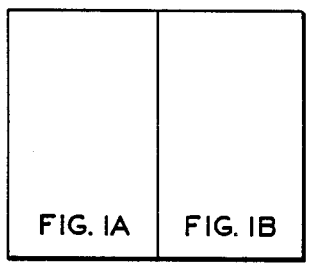
FIG. 1 illustrates the relationship of FIGS. 1A and 1B of the present invention.
Figure 1A:
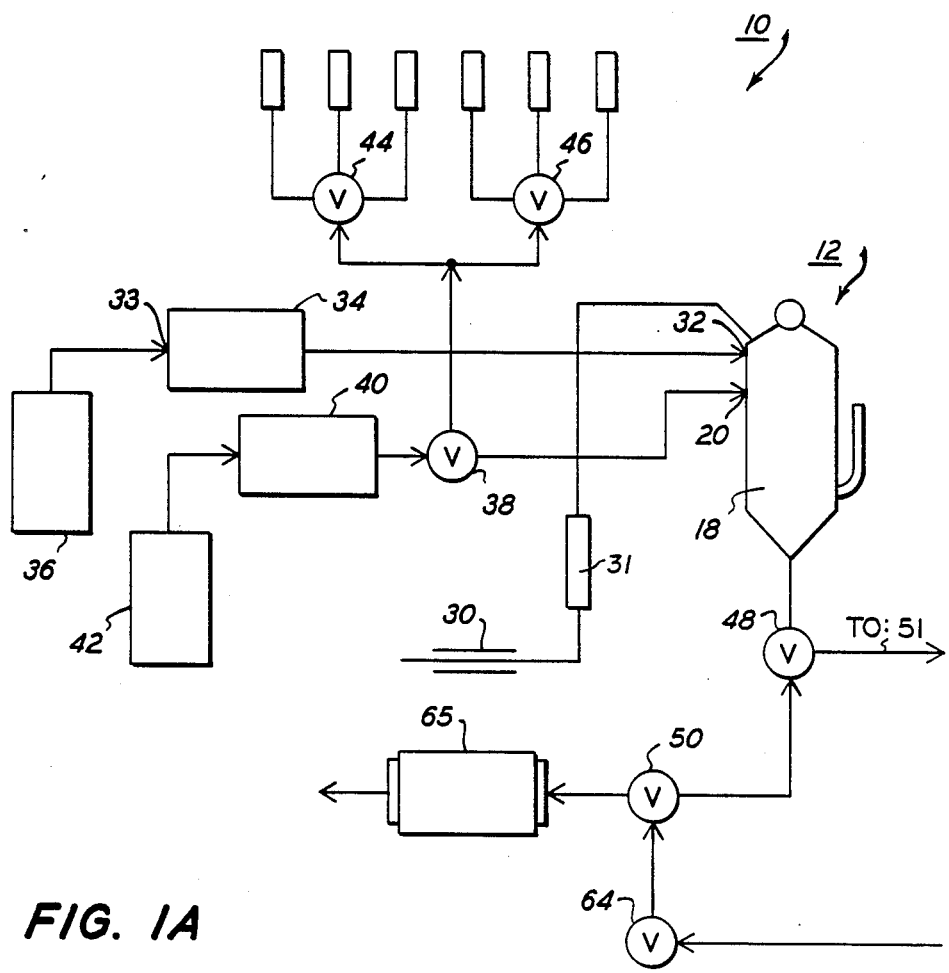
FIG. 1A is a diagram of the automatic feed system an apparatus of the present invention.
Figure 1B:
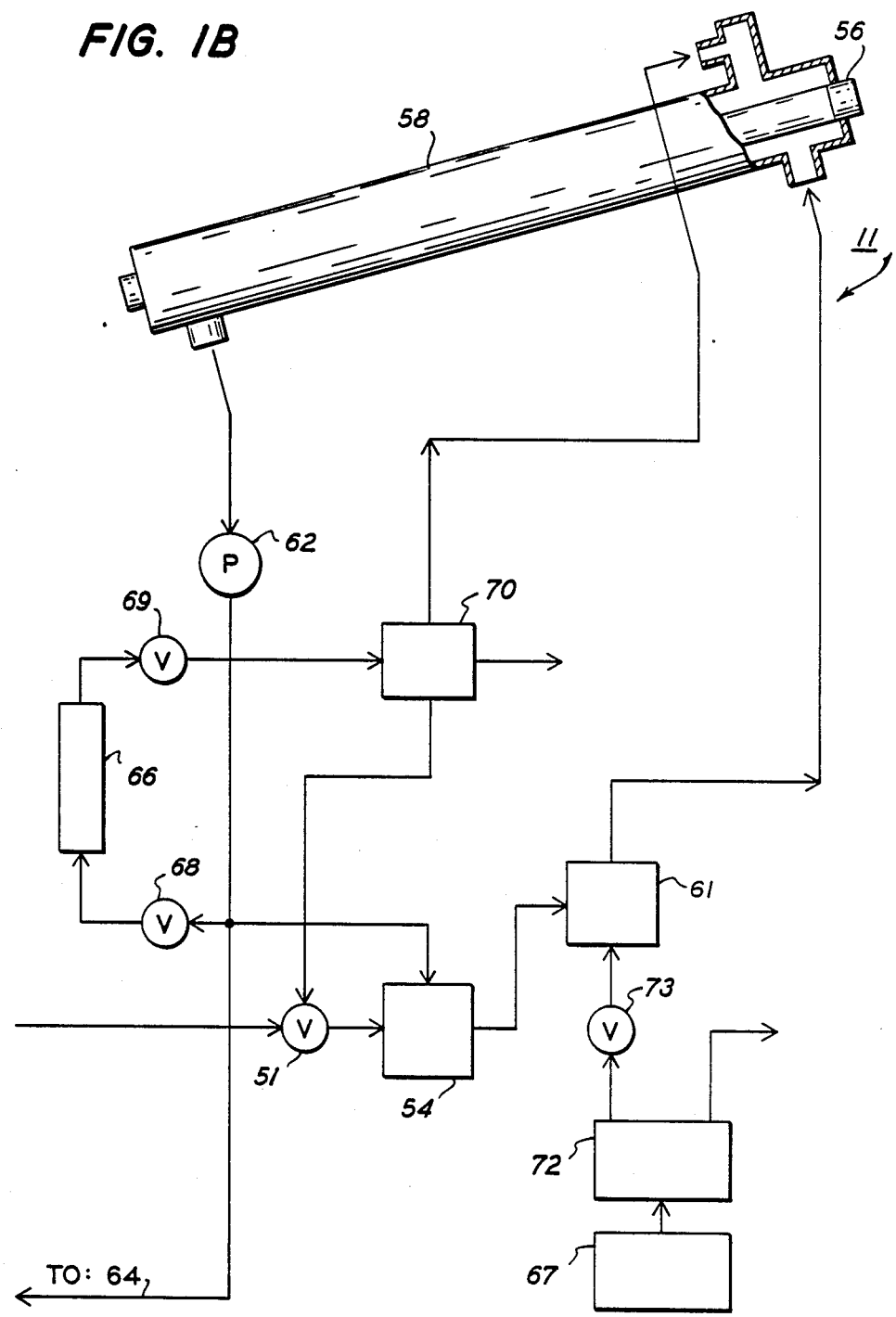
FIG. 1B is a diagram of the organic carbon analyzer system of the apparatus of the present invention.

Referring to FIG. 1A, there is illustrated an automatic feed system 10 for and selectively introducing successive samples of a liquid into the organic carbon analyzer 11 illustrated in FIG. 1B. The organic carbon analyzer system 11 of the present invention is substantially identical to the process for measuring the content of organic carbon illustrated and described in U.S. Pat. No. 3,958,941 previously referred to and which is hereby incorporated by reference and operates in the same manner as the device described in the U.S. Pat. No. 3,958,941, with the only difference being that in the particular embodiment illustrated a persulfate reservoir is provided which is in communication with a pump for introduction the persulfate in the main measuring loop. The addition of persulfate contributes to the efficiency of the carbon analyzer system 11.

Figure 4:
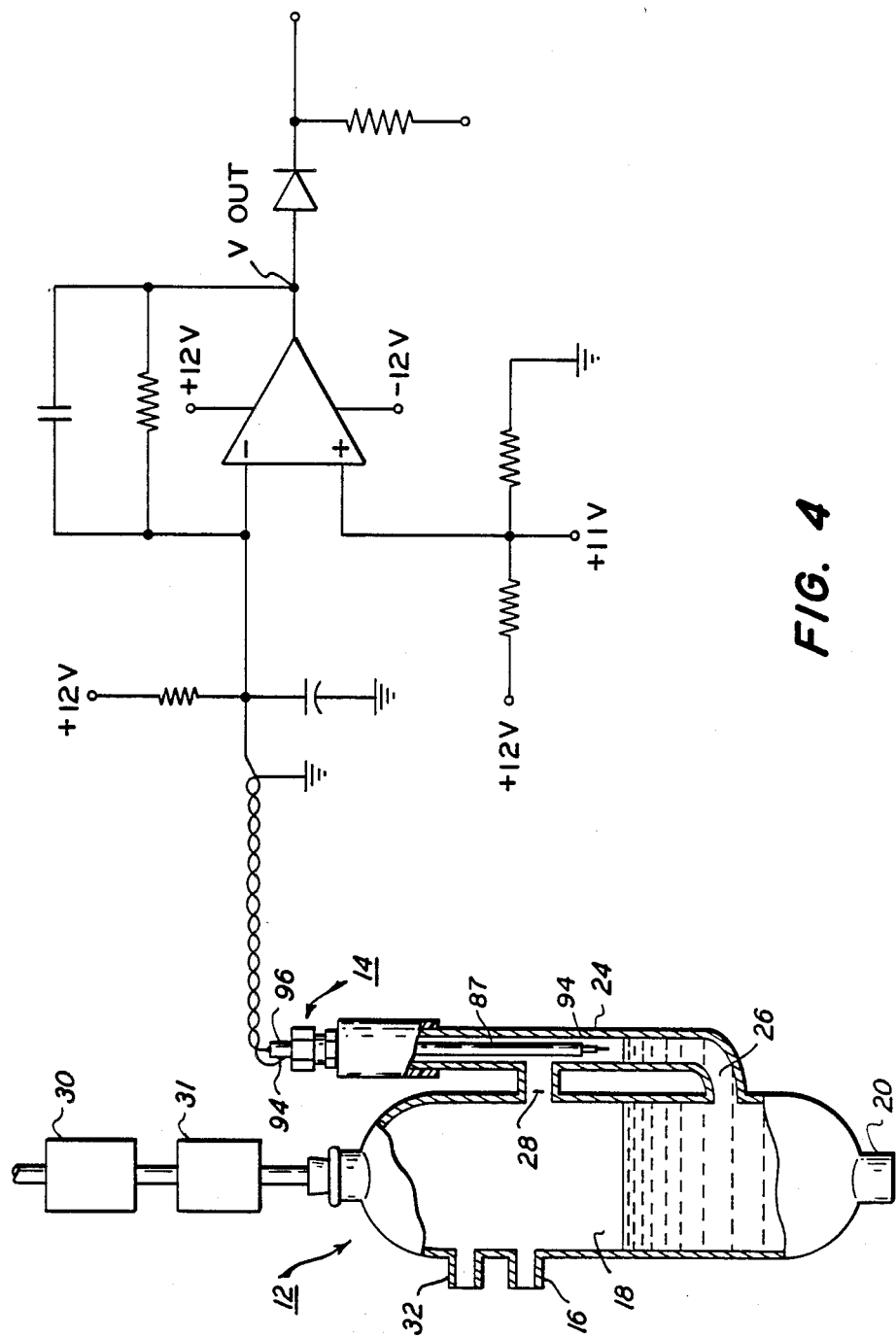
FIG. 4 is a plan view of the funnel of FIG. 2 illustrating the level sensor and the electrical circuitry used with the level sensor.

Referring to FIGS. 1A, 1B and 4 the automatic feed system 10 comprises a receiving funnel 12 having a main receiving chamber 18, an integrally formed inlet port 16 which is in direct communication with receiving chamber 18 and an integrally formed outlet port 20 which is also in communication with the main receiving chamber 18. The main receiving funnel 12 is further provided with air filters 30, 31 (see FIG. 4) which are in communication with the main receiving chamber 18 exhaust port 35 so as to allow air to enter or exit from the main receiving chamber 18 in response to the level of the liquid therein while minimizing the introduction of impurities. Filters 30, 31 generally comprises a filter 30 for removing carbon dioxide ($CO_2$) and a filter 31 for removing organic impurities in the air. Receiving funnel 12 further includes a measuring chamber 24 which is direct communication with main receiving chamber 18 through passageways 26, 28. Passageway 28 is provided at a position vertically above passage 26 such that liquid in the main receiving chamber easily flows in the measuring chamber while allowing air to leave the measuring chamber and thereby minimize the transmission turbulence from the the main receiving chamber 18 into measuring chamber 24.

The receiving funnel 12 is further provided with a second integrally formed inlet port 32 which is also in direct communication the main receiving chamber 18. The second inlet port 32 is in direct communication with the outlet of reagent pump 34. Reagent pump 34 has an inlet 33 which is in direct communication with reagent reservoir 36. When the reagent pump 34 is activated it pumps a liquid reagent from reagent reservoir 36 into receiving funnel 12.

The first inlet port 16 is in direct communication with the outlet of funnel valve 38. Funnel valve 38 has 2 inlet ports which allow communication with the outlet of funnel valve 38. One of said inlet ports of said funnel valve 38 is in direct communication with the outlet of standard pump 40. Standard pump 40 has an inlet which is in direct communication with standard reservoir 42.

Standard reservoir 42 holds a liquid solution which is used to calibrate the organic measuring apparatus 11.

The second inlet port of said funnel valve 38 is in direct communication with the process line valves 44 and 46. In the particular embodiment illustrated, each process feedline valve has 3 inlet ports connected to a different process feedline. Therefore, in the present invention, the process feedline valves 44, 46 are connected to 6 process lines. There may, of course, be any desired number of process feedlines and any number of different connections may be provided to each valve. Each connection may represent a totally different process feedline being monitored or a different point in the manufacturing process of a single process line.

Referring to FIGS. 2, 3, and 4, level sensor 14 is positioned within measuring chamber 24 through opening 72. Around the outside of the opening 72 there is provided a heat shrink tubing 81 for receiving therein an adapter 82 which is permanently held in position to connector 83. A thermal plastic rubber spacer 84 is positioned within connector 83 having an opening therethrough for receiving first electrode 87. In the particular embodiment illustrated first electrode 87 comprises a hollow tube preferably made of stainless steel. A nut 85 is threadably engagable with connector 83. The nut 85 may be turned about its axis with respect to connector 83 so as to cause relatively vertical movement between the two pieces. Within the electrode 87 there is provided a second electrode 86 which is spaced from first electrode 87 by insulator 88. In the particular embodiment illustrated insulator 88 is made of a teflon type material and second electrode 86 is a silver plated wire. Second electrode 86 and the first electrode 87 extend into the receiving chamber 24 below second passageway 28. Insulator 88 extends at least to the end 92 of first electrode 87. The wire 86 passes through the level sensor assembly extending beyond the end 92 of first electrode 87. The axially outer ends 94, 96 of of tube 84 and wire 86, respectively, are electrically connected to the amplifying circuit as illustrated in FIG. 4. The circuit illustrated in FIG. 4 produces an appropriate electrical signal to the electronics of the apparatus to turn on or off the appropriate valves and/or pumps.

The present invention is particularly adapted for measuring the organic content of ultrapure water. Generally ultrapure water has organic impurities less than about 100 parts/billion. Additionally ultrapure water has a resistivity approaching 18 million ohm-cm which is quite high. Therefore, contamination, which can significantly affect the resistivity of the aqueous liquid is an important factor. In order to minimize contamination receiving funnel 12 is preferably made of an inert material. In the particular embodiment illustrated receiving funnel 12 is made of glass. The parts of the automatic feed system 10 are also made of a material which produces low contamination. In the present invention all valves are made of teflon or are teflon coated. The level sensor of the present invention has been designed to minimize contamination of the ultra pure water. As previously noted first electrode 87 is made of stainless steel and second electrode 86 is a silver coated wire.

The automatic supply system 10 is further provided with a divert valve 48 which is in direct communication with the outlet port 20 of receiving funnel 12. Divert valve 48 has one exit/entrance port connected to divert backfill valve 50. The divert valve 48 has a another port which is direct communication with a aspirate valve 51 which is direct communication with the primary loop of the organic carbon measuring system 11. Divert backfill valve 50 has an outlet which is in direct communication with divert pump 65 which empties to drain. Divert backfill valve 50 has another inlet/exit port which is in direct communication with backfill valve 64 which is in direct communication with the primary loop of organic carbon measuring system 11. Backfill valve 64 is normally in the closed state.

The organic measuring system 11 includes an eductor 54 and ultraviolet lamp 56 enclosed in an irradiation chamber 58. Eductor 54 is in direct communication with the septum block 61 which in direct communication with irradiation chamber 58. The other end of irradation chamber 58 is connected to a main pump 62 which is in communication with backfill valve 64. Main pump 62 is also in direct communication with solenoid valve 68 which is in direct communication with a deionization filter cartridge 66. Main pump 62 is also in communication with eductor 54 previously discussed as illustrated. The organic carbon measuring system 11 further includes a measuring chamber 70 in communication with irradiation chamber 58 and the deionization filter 66 through solenoid valve 69. A persulfate reservoir 67 is in communication with the inlet of persulfate pump 72 which has an outlet in direct communication with a poppet valve 73 which is in communication with septum block 61 through poppet valve 73. As previously stated the organic carbon measuring system 11 operates in the same manner as the organic measuring system illustrated in U.S. Pat. No. 3,958,941 which has been incorpoated herewith. The only difference between the measuring system, of U.S. Pat. No. 3,955,941 and present invention as previously discussed, is the addition of a persulfate reservoir which is dispensed during the measuring cycle. The actual measuring and operation of the organic carbon measuring system is in all other respects identical.

In order to more fully understand how the present invention operates, an operational cycle of the automatic supply system 10 will be described. The electronics of the apparatus is such that the appropriate valves and/or pumps are activated so that the desired process feedline becomes in direct communication with the receiving funnel 12 thereby allowing an aqueous solution to flow through valve 44 or 46 through funnel valve 38 into receiving chamber 18. In the present invention, the process lines are under pressure, therefore, no addtional pump is necessary, however, if the liquid to be analyzed is not under pressure, a pump may be provided if required. Flow from the process feedline through inlet port 16 will be automatically shut off when the level within the funnel valve reaches a predetermined set amount. When liquid contact is made between the two electrodes of the level sensor, an appropriate electrical signal is produced which turns off the process feedline valves and funnel valve. After this is done the electronics sends the appropriate signal to reagent pump 34 which introduces a specified quantity of reagent into main receiving chamber 18 to be mixed with the sample to be measured. This is accomplished by reagent pump 34 being of the metering type. Therefore, by knowing the rate at which the pump 34 operates the reagent pump 34 is turned on for the appropriate time period so as to introduce the desired amount of reagent. While the receiving funnel is being filled with the appropriate amount of sample, divert valve 48 is in the closed position and thereby maintains the liquid sample in the receiving funnel 12. After an appropriate amount of reagent is put into the funnel, the reagent pump is turned off. The divert and aspirate valves are then opened so as to provide communication between the main receiving funnel and primary measuring loop of measuring system 11 through eductor 54. An important aspect of the present invention is that the automatic feed system 10 permits automatic calibration of the organic carbon analyzer. In order to make the appropriate calibration adjustments to the organic carbon analyzing system 11, a predetermined amount of a standard solution is analyzed in the carbon analyzer system 11. This standard solution is first introduced into the receiving funnel 12. The standard solution is then supplied to the organic carbon system 11 so that an initial organic carbon reading can be taken from a known quantity. Here again the level sensor 14 provides the appropriate signal for turning off the standard pump 40 and funnel valve 38. A sample of the water in the main loop is then analyzed and the background level of organic carbon is determined. This value is compared with the measurement taken from the standard solution. Then the apparatus is appropriately recalibrated to account for any difference in measurement. Thereafter various samples from the feedline can be individually analyzed. It is, of course, understood that the sequence of samples to be analyzed from the various feedlines may be preset to be taken in any order so desired. Therefore, the feedlines may be taken in sequential order or certain feedlines may be analyzed more often than others.

The present system is designed to minimize contamination between different samples placed in receiving funnel 12. This is accomplished by providing a flushing cycle between samples. That is before divert valve is closed, an appropriate amount of sample is allowed to pass through funnel 12 through divert backfill valve 50, divert pump 65 to drain. Therefore before a sample is analyzed, a certain amount of the sample is passed through to drain to remove traces of the prior sample. This flushing process can be done each time a different ingredient or sample is placed within the receiving funnel 12.

Referring to FIG. 4, there is illustrated funnel 18 and the electrical diagram of the electronics necessary to measure the conductivity of the ultrapure water being introduced into the funnel 12. Since the process feedlines contain ultrapure water, the restivity of the water is quite high, accordingly the conductivity is quite low. The wire 86 is connected to ground where the first electrode 87 is connected to the negative side of an Fairchild amplifier UA348. The positive side of the Fairchild amplifier is connected between two resistors, a one (1) meg ohm resistor and 12 meg ohm resistor. The other side of the 12 meg ohm resistor is connected to ground and the other side of the 1 meg ohm resistor is connected to a 12 volt source. The feedback circuit of the output 1 of the amplifier is connected to the negative side of the amplifier wherein a 12 meg ohm and 0.01 microfard capacitor are placed in parallel. Between the negative input of the amplifier and the 12 volt power source there is provided a 1 meg ohm resistor. A 0.01 (uf) microfarad capacitor is placed between the negative side of the amplifier and ground. Connected to the voltage output of the amplifier is a diode which is electrically connected to 100K resistor which is connected to ground. The output signal may be taken off from the circuit after the diode as indicated. This circuit is set up as a comparator with a gain of 12 volts. The reference voltage is set to approximately 11 volts. When the liquid in the measuring chamber is not touching the tube 87, the signal is at 12 volts, one volt above the reference voltage and since the amplifier is biased with a negative gain of 12, the voltage output is minus 12.8 volts. The diode now remains off since it is reversed biased and the signal output voltage remains at ground or zero volts. When the water reaches this stainless steel tube 87 and a liquid connection is made between the wire and pipe, the input biasing current of the amplifier is diverted to ground through the water causing the amplifier to swing to 12.8 volts. This forward biases the diode and cancels the signal output volt from zero to 12 volts.

We claim:

1. An apparatus for measuring the amount of dissolved organic carbon introduced into a quantity of ultra pure carrier water, said apparatus comprising:
   a first housing;
   a water pump;
   a first water loop containing a quantity of ultral pure carrier water, including and interconnecting said pump and said frist housing for continuously circulating the quantity of ultra pure carrier water;
   means for automatically introducing a liquid sample having dissolved organic carbon liquid into said first water loop;
   an ultraviolet lamp in ultraviolet communication with an interior of said first housing for irradiating dissolved organic carbon present in said first housing:
   a second housing;
   a second loop interconnecting said first housing and said second housing for transferring a portion of carbon dioxide produced in said first housing into said second housing and for supplying oxygen to said first housing;
   measurement means for measuring an amount of carbon dioxide in said second housing, the amount of carbon dioxide being representative of an amount of organic carbon introduced into the apparatus;
   said means for automatically introducing samples having dissolved organic carbon into said first water loop comprising:
   a recieving funnel having an outlet port, at least one inlet port connected to a pressurized line, an exhaust port for allowing air to enter or exit said funnel, a main receiving chamber for receiving said at least one inlet port and means defining a measuring chamber connected to the main receiving chamber by first and second passageways, said second passageway being positioned vertically above said first passageway to allow air to leave the measuring chamber thereby minimizing turbulence from said main chamber into said measuring chamber, said measuring chamber having a bottom end and a top outer end;
   means for controlling flow of a liquid to said funnel through said at least one inlet port;
   means for selectively maintaining liquid samples in said receiving funnel and emptying liquid samples from said funnel through said outlet port;
   said means for maintaining liquid samples in said receiving funnel and for emptying said receiving funnel comprising a first valve means in direct communication with said outlet port of said receiving funnel; said first valve means being in communication with an organic carbon measuring portion of said apparatus and with a second valve means which is in direct communication with a divert pump which empties to a drain;

filter means connected to said exhaust port for minimizing introduction of impurities resulting from air entering or leaving said funnel in response to a level of liquid sample in said funnel;

means for sensing a level of said liquid sample being maintained in said measuring chamber comprising a first electrode, a second electrode spaced from said first electrode, said first and second electrodes being electrically connected to an amplifier for sensing conductivity of a medium between said first and second electrodes such that when a predetermined change in conductivity between said first and second electrodes is reached, said amplifier produces a response signal for stopping flow of liquid sample into said funnel, said first electrode comprising a cylindrical tube having an inner end directed to said bottom end of said measuring chamber and an outer end directed to the top end of said measuring chamber, said second electrode comprising a wire having an inner end which extends through said tube beyond said inner end of said tube, an insulating material disposed between said tube and said wire, said insulating material extending beyond the inner end of said tube but short of the inner end of said wire.

2. An apparatus for measuring the amount of dissolved organic carbon introduced into a quantity of ultra pure carrier water, said apparatus comprising:

a first housing;

a water pump;

a first water loop containing a quantity of ultra pure carrier water, including and interconnecting said pump and said first housing for continuously circulating the quantity of ultra pure carrier water;

means for automatically introducing a liquid sample having dissolved organic carbon liquid into said first water loop;

an ultraviolet lamp in ultraviolet communication with an interior of said first housing for irradiating dissolved organic carbon present in said first housing;

a second housing;

a second loop interconnecting said first housing and said second housing for transferring a portion of carbon dioxide produced in said first housing into said second housing and for supplying oxygen to said first housing;

measuring means for measuring an amount of carbon dioxide in said second housing, the amount of carbon dioxide being representative of an amount of organic carbon introduced into the apparatus;

means for automatically introducing samples having dissolved organic carbon into said first water loop comprising:

a receiving funnel having an outlet port, at least one inlet port connected to a pressurized line, an exhaust port for allowing air to enter or exit said funnel, a main receiving chamber for receiving samples from said at least one inlet port and means defining a measuring chamber connected to the main receiving chamber by first and second passageways, said second passageway being positioned vertically above said first passageway to allow air to leave the measuring chamber thereby minimizing turbulence from said main chamber into said measuring chamber, said measuring chamber having a bottom end and a top outer end;

means for controlling flow of a liquid to said funnel through said at least one inlet port;

means for selectively maintaining liquid samples in said receiving funnel and emptying liquid samples from said funnel through said outlet port;

said means for maintaining liquid samples in said receiving funnel and for emptying said receiving funnel comprising a first valve means in direct communication with said outlet port of said receiving funnel; said first valve means being in communication with an organic carbon measuring portion of said apparatus and with a second valve means which is in direct communication with a divert pump which empties to drain;

filter means connected to said exhaust port for minimizing introduction of impurities resulting from air entering or leaving said funnel in response to a level of liquid sample in said funnel;

means for sensing a level of liquid sample being maintained in said measuring chamber comprising a first electrode, a second electrode spaced from said first electrode, said first and second electrodes being electrically connected to an amplifier for sensing conductivity of a medium between said first and second electrodes such that when a predetermined change in conductivity between said first and second electrodes is reached, said amplifier produces a response signal for stopping flow of liquid sample into said funnel.

3. An organic carbon measuring apparatus for automatically measuring successive samples of an ultra pure liquid having a low conductivity, said apparatus comprising;

a receiving funnel having an outlet port, at least one inlet port connected to a pressurized line and an exhaust port for allowing air to enter or exit said funnel, a main receiving chamber for receiving samples from said at least one inlet port and means defining a measuring chamber connected to the main receiving chamber by first and second passageways, said second passageway being positioned vertically above said first passageway to allow air to leave the measuring chamber thereby minimizing turbulence from said main chamber into said measuring chamber, said measuring chamber having a bottom end and a top outer end;

means for controlling flow of a liquid to said funnel through said at least one inlet port;

means for selectively maintaining liquid samples in said receiving funnel and emptying liquid samples from said funnel through said outlet port comprising a first valve means in direct communication with said outlet port of said receiving funnel, said first valve means being in communication with an organic carbon measuring portion of said apparatus and with a second valve means which is in direct communication with a divert pump which empties to a drain;

first means connected to said exhaust port for minimizing introduction of impurities resulting from air entering or leaving said funnel in response to a level of liquid samples in said funnel, means for sensing a level of liquid sample being maintained in said measuring chamber comprising a first electrode, a second electrode spaced from said first electrode, said first and second electrodes being electrically connected to an amplifier for sensing conductivity of a medium between said first and second electrodes such that when a predetermined change in conductivity between said first and second electrodes is reached, said amplifier produces a response signal for stopping flow of liquid sample into said funnel;

said first electrode comprising a cylindrical tube having an inner end directed to said bottom end of said measuring chamber and an outer end being directed to the top end of said measuring chamber and extending through an opening at the top end of said measuring chamber, said second electrode comprising a wire having an inner end which extends through said tube beyond said inner end of said tube, an insulating material disposed between said tube and said wire, said insulating material extending beyond the inner end of said tube but short of the inner end of said wire.

4. An orgaic carbon measuring apparatus for automatically measuring successive samples of an ultra pure liquid having a low conductivity, said apparatus comprising;

a receiving funnel having an outlet port, at least one inlet port connected to a pressurized line, an exhaust port for allowing air to enter or exit said funnel, a main receiving chamber for receiving samples from said at least one inlet port and means defining a measuring chamber connected to the main receiving chamber by first and second passageways, said second passageway being positioned vertically above said first passageway to allow air to leave the measuring chamber thereby minimizing turbulence from said main chamber into said measuring chamber, said measuring chamber having a bottom end and a top outer end;

means for controlling flow of a liquid to said funnel through said at least one inlet port;

means for selectively maintaining liquid samples in said receiving funnel and emptying liquid samples from said funnel through said outlet port;

said means for maintaining liquid samples in said receiving funnel and for emptying said receiving funnel comprising a first valve means in direct communication with said outlet port of said receiving funnel, said first valve means being in communication with an organic carbon measuring portion of said apparatus and with a second valve means which is in direct communication with a divert pump which empties to a drain;

filter means connected to said exhaust port for minimizing introduction of impurities resulting from air entering or leaving said funnel in response to a level of liquid sample in said funnel;

means for sensing a level of liquid sample being maintained in said measuring chamber comprising a first electrode, a seocnd electrode spaced form said first electrode, said first and second electrodes being electrically connected to an amplifier for sensing conductivity of a medium between said first and second electrodes such that when a predetermined change in conductivity between said first and second electrodes is reached, said amplifier produces a response signal for stopping flow of liquid sample into said funnel.

5. An appratus according to claim 4 wherein said first electrode comprises a cylindrical tube having an inner end directed toward the bottom end of said measuring chamber and an outer end being directed toward the top end of said measuring chamber and extending through an opening in the top end of said measuring chamber, said second electrode comprising a wire having an inner end which extends through said tube beyond said inner end of said tube, and wherein an insulating material is disposed between said tube and said wire with said insulating material extending beyond the inner end of said tube but stopping short of the inner end of said wire.

6. An apparatus according to claim 4, wherein said means for controlling flow of liquid to said funnel comprises a third valve means having an exit port in direct communication with said at least one inlet port of said funnel, a first inlet port in communication with one of said at least one inlet ports connected to pressurized process feedlines, a second inlet port in direct communication with a first pump which is connected to a first reservoir, said first inlet port of said third valve means also being connected to a fourth valve means having at least one process line connected thereto.

7. An apparatus according to claim 4 wherein said receiving funnel has a second inlet port in direct communication with a second pump, the inlet of said second pump being in direct communication with a second reservoir.

* * * * *